U S007751904B2

(12) United States Patent
Pasquantonio

(10) Patent No.: US 7,751,904 B2
(45) Date of Patent: Jul. 6, 2010

(54) ELECTRODE LEAD FOR IMPLANTATION INTO A SMALL HEART VESSEL

(75) Inventor: Jay Pasquantonio, Damascus, OR (US)

(73) Assignee: Biotronik CRM Patent AG, Baar (CH)

(*) Notice: Subject to any disclaimer, the term of this patent is extended or adjusted under 35 U.S.C. 154(b) by 250 days.

(21) Appl. No.: 11/947,513

(22) Filed: Nov. 29, 2007

(65) Prior Publication Data

US 2009/0143847 A1    Jun. 4, 2009

(51) Int. Cl.
*A61N 1/05* (2006.01)
(52) U.S. Cl. ..................................... 607/122
(58) Field of Classification Search ............... 607/122; 604/528
See application file for complete search history.

(56) References Cited

U.S. PATENT DOCUMENTS

| | | | |
|---|---|---|---|
| 5,303,704 A | | 4/1994 | Molacek et al. |
| 5,935,159 A | * | 8/1999 | Cross et al. ............ 607/116 |
| 2002/0183822 A1 | * | 12/2002 | Bodner ................. 607/122 |
| 2004/0082986 A1 | * | 4/2004 | Westlund et al. ....... 607/122 |
| 2005/0203599 A1 | * | 9/2005 | Garabedian et al. .... 607/116 |
| 2006/0009829 A1 | * | 1/2006 | Aron et al. ............. 607/122 |
| 2007/0106144 A1 | | 5/2007 | Squeri |

FOREIGN PATENT DOCUMENTS

| | | |
|---|---|---|
| WO | WO 01/91851 | 12/2001 |
| WO | WO 01/91851 A1 * | 12/2001 |

OTHER PUBLICATIONS

European Search Report, dated Mar. 18, 2009.

* cited by examiner

*Primary Examiner*—George R Evanisko
*Assistant Examiner*—Andrew Hayes
(74) *Attorney, Agent, or Firm*—ARC IP Law, PC; Joseph J. Mayo

(57) ABSTRACT

An electrode lead for implantation into a small heart vessel, especially into a coronary sinus, is provided with an elongated outer insulating lead body (1), having a proximal end (2), a distal end (3) and at least one electrode pole (4) at the distal end (3). At least one electrical conductor unit (6, 6') leads to said electrode pole (4), each of said electrical conductor units (6, 6') having a conductor core (7) and a separate insulating sheath (8) surrounding said conductor core (7). A lumen (9) is provided in said insulating lead body (1), being defined by a tubular envelope (10), to accommodate a guide wire means (11). The at least one electrical conductor unit (6, 6') and the envelope (10) of the lumen (9) are each slidable relative to each other along their longitudinal direction (L) and fixed relative to each other at least in the vicinity of the distal end (3) of the lead body (1).

16 Claims, 1 Drawing Sheet

ELECTRODE LEAD FOR IMPLANTATION INTO A SMALL HEART VESSEL

BACKGROUND OF THE INVENTION

1. Field of the Invention

The invention relates to an electrode lead for implantation into a small heart vessel, especially into e.g. the coronary sinus, comprising an elongated outer insulating lead body having a proximal end, a distal end and at least one electrode pole at the distal end, further comprising at least one electrical conductor unit for said electrode pole, each of said electrical conductor units having a conductor core and a separate insulating sheath surrounding said conductor core, and a lumen in the insulating body.

2. Description of the Related Art

Electrode leads of the above type are well known from the prior art. They serve as an electrical connection between an electrotherapeutic implantable device, which may be e.g. a pacemaker, and the location being treated in the body. By means of the electrode pole at the distal end of the lead e.g. a stimulation pulse can be applied to the cardiac tissue or electrical heart signals can be measured. When such an electrode lead is to be implanted in small heart vessels, like coronary venous vessels, there rise specific problems which are to be discussed as follows:

When the vessel scheduled to accommodate the electrode lead is too small another vessel must be found the dimensions of which are sufficient to receive the lead. If this is not possible the implantation procedure must be abandoned in favour of surgical implantation of e.g. an epicardial lead.

When the electrode lead is too difficult to handle or the placement of the lead is sophisticated or even impossible this again might give reason to epicardial lead surgery or an inadequate placement of the electrode lead. The latter results in an insufficient or at least suboptimal therapeutic performance as concerns e.g. resynchronization.

Basically known electrode leads comprise a steering mechanism with at least one pull wire running in a lumen of the lead body. By pulling this wire at the proximal end of the lead body the distal end can be bended. Thus by rotating the lead body around its longitudinal axis the distal tip of the lead body can be controlled in his position and direction and thus can be fed into a small vessel at a vein branch.

It is a matter of fact that this steering mechanism demands a certain space within the sectional contour of the lead body which is contrary to the requirement of miniaturizing the electrode lead to facilitate the placement in small heart vessels.

BRIEF SUMMARY OF THE INVENTION

Therefore it is an object of the invention to provide for a steerable electrode lead with a cross sectional area as small as possible and based on a simple construction.

This object is achieved by an electrode lead wherein the at least one electrical conductor unit and the envelope of the lumen are each slideable relative to each other along their longitudinal direction and fixed relative to each other in the vicinity of the distal end of the lead body.

By making the at least one electrical conductor unit and the envelope of the lumen moveable independently of each other except at the tip, steerability of the electrode lead is achieved without any mechanism solely designed for steerability. Thus an increase of the cross section area of the electrode lead due to construction elements for the steering mechanism is totally avoided. This decisively helps to miniaturize the electrode lead. The functionality of the inherent steering mechanism of the invention is discussed in connection with the explanation of the drawing figures below.

According to a preferred embodiment of the invention the at least one electrical conductor unit and the envelope of the lumen are attached in a side-by-side relationship parallel to each other, the entirety of the at least one electrical conductor unit and the envelope of the lumen being encased by the lead body. Inasmuch the traditional concept of symmetry in electrode lead construction is left behind. The key concepts of the invention differentiate left ventricular (coronary sinus) lead design from traditional pacing leads. The first concept is that reliable sensing is not required for a left ventricular lead, so said coaxial and coradial design is unnecessary to prevent noise rejection within the lead. The second concept is that symmetry in the lead's diameter is unnecessary or undesirable for placement and fixation. Asymmetry in the lead may improve steerability and trackability for lead placement and shape retention for stability.

According to a further preferred embodiment of the invention the lead body comprises flat outer surface regions. Together with the above mentioned internal structures which run parallel to each other the result is a lead with the mechanical properties most closely resembling a ribbon with excellent torque transmission.

Another preferred embodiment of the invention is directed to a fixation of the at least one electrical conductor unit and the envelope in the vicinity of the proximal end of the lead body. This helps to improve the efficiency of the inherent steering mechanism as becomes clear from the description of the drawing figures.

To enhance the mobility of the internal structures relative to each other the insulating sheath of the at least one electric conductor unit and the tubular envelope of the lumen are made of PTFE polymer having a low friction surface. Furthermore the insulating lead body is provided with a low friction inner surface e.g. by means of a thin polyurethane coating on the silicone insulating lead body.

Summing up compared to prior art electrode leads for implantation into small heart vessels the leads according to the invention are much smaller and are steerable without the use of e.g. a shaped stylet, guide wire or other external mechanism. This allows the implanter to access and fixate the leads in much smaller vessels than it is achievable with existing coronary sinus leads.

DETAILED DESCRIPTION OF THE INVENTION

Figure 1:
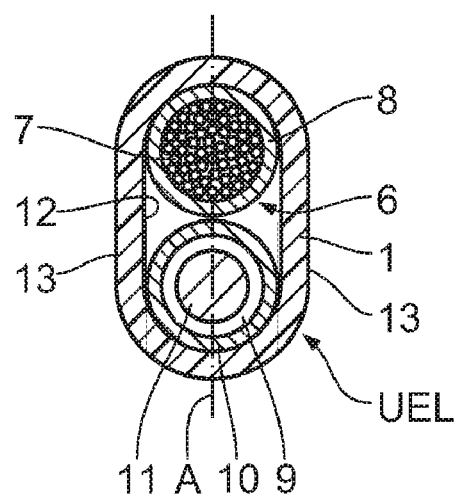
FIG. 1 is a cross section view of an electrode lead in a first embodiment.
Figure 2:
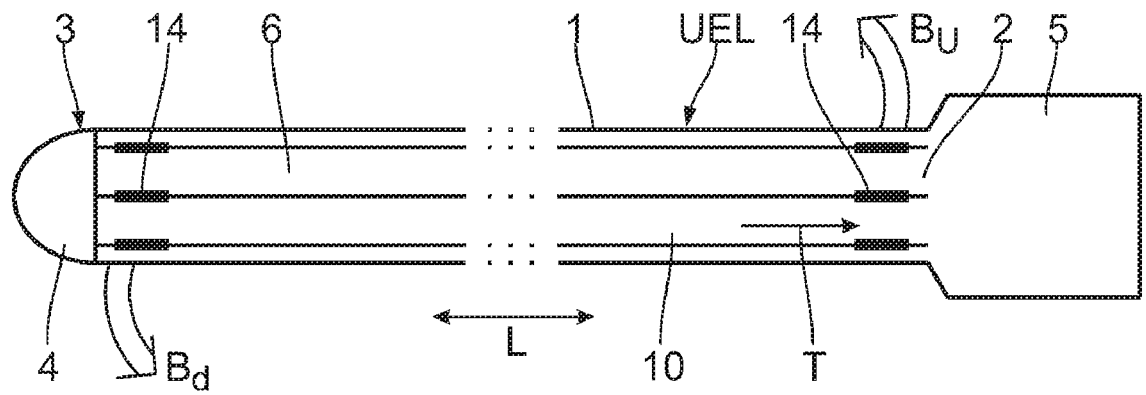
FIG. 2 is a schematic side elevation of the electrode lead according to FIG. 1.

Referring to FIGS. 1 and 2 an unipolar electrode lead UEL for left ventricular implantation, e.g. into the coronary sinus, comprises an elongated outer insulating lead body 1 having a proximal end 2, a distal end 3 and an electrode pole 4 at the distal end tip of the lead body 1. As can be seen from FIG. 2 the proximal end 2 of the UEL is provided with a common connector 5 to connect the electrode lead UEL to e.g. a pacemaker implanted into a patient's body.

To connect the electrode pole 4 to the connector 5 an electrical conductor unit 6 is provided which comprises a conductor core 7, e.g. made of a metallic strand, and an insulating sheath 8 surrounding the conductor core 7.

In a side-by-side relationship and parallel to said conductor unit 6 a lumen 9 is defined by a tubular envelope 10. Within this lumen 9 a guide wire 11 can be located as is depicted in FIG. 1.

The lead body 1 is made of an insulating silicone material which on its inner surface 12 is provided with a low friction coating made of thin polyurethane. Both the insulating sheath 8 of the conductor unit 6 and the tubular envelope 10 of the lumen 9 are made of a PTFE polymer which due to its material properties has a very slick surface. Accordingly all construction elements of the electrode lead being arranged side-by-side in a parallel arrangement are slideable relative to each other along their longitudinal direction L in principle. As is depicted in FIG. 2, however, the conductor unit 6 and the tubular envelope 10 are fixed by an adequate fixation means 14, like a glue point, relative to each other at the distal end 3 and also to the proximal end 2 of the electrode lead. The relative slidability of the conductor unit 6 and the tubular envelope 10 on the one hand and aforesaid fixations 14 of these construction elements at the proximal and distal end 2, 3 of the electrode lead give rise to an inherent steering mechanism for the electrode lead which requires no separate construction elements, as becomes clear from the following:

When an implanter—as is indicated in FIG. 2 by the arrow $B_u$—bends the lead body 1 in an upward direction in the axial plane A then a tension force T is generated in the tubular envelope 10 due to the larger bending diameter of this construction element compared to the conductor unit 6. This tension force T can be transmitted to the distal end 3 as both the conductor unit 6 and the tubular envelope 10 are slideable relative to each other and to the lead body 1. This tension force T causes the lead body 1 at its distal end 3 to bend down in the direction $B_d$.

As can be seen from the foregoing the electrode lead according to the invention presents a fine steerability of the distal end 3 for placement of the lead UEL in e.g. the side branches of the coronary veins or for a direction of the tip for an advancement of the guide wire down such a side branch.

As concerns the overall cross section form of the electrode lead UEL FIG. 1 indicates that the outer insulating lead body 1 comprises flat outer surface regions 13 which run parallel to the axial plane A mentioned above. Accordingly the unipolar electrode UEL has a substantially flat rectangular outer sectional contour which is rounded at opposing side parts.

Figure 3:
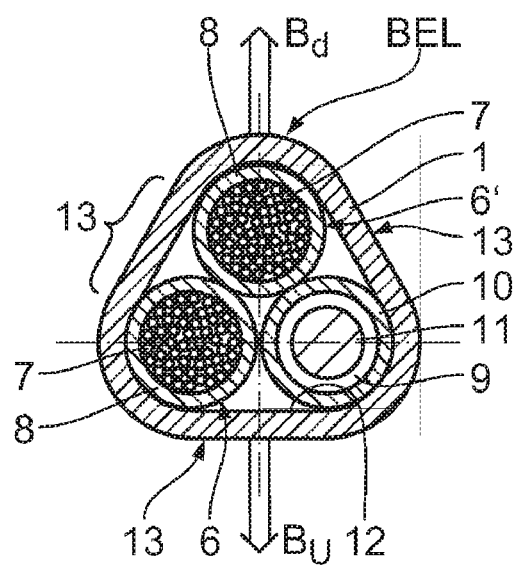
FIG. 3 is a cross section view of an electrode lead in a second embodiment.

FIG. 3 shows a second embodiment of the invention which is a bipolar electrode lead BEL having a tip electrode pole and a ring pole at the distal end 3 what is well-known from prior art. This electrode configuration allows e.g. bipolar sensing. The electrical connection between the lead poles and the connector is in this case assured by two connector units 6, 6' which comprise a strand core 7 and an insulating sheath 8 made of PTFE polymer again. Furthermore, a lumen 9 defined by a tubular envelope 10 is arranged nearby the conductor units 6, 6'. As can be seen from FIG. 3 these elements 6, 6', 10 are arranged in a triangular configuration parallel to each other within the insulating lead body 1 whereby the lead body 1 forms three flat outer regions. All of these flat outer regions are nearly of the same form. Therefore the bipolar electrode lead BEL has a substantially triangular outer cross section contour with three flat outer surface regions 13 of nearly the same form.

Again all construction elements are on the one hand slideable relative to each other, but on the other hand fixed at the distal and proximal end. Thus again by bending the lead body 1 e.g. upwards in direction of one flat outer surface region which is built up by the connector unit 6 and the tubular envelope 10 at the proximal end 2 (arrow $B_u$ in FIG. 3) leads to a downward bending $B_d$ at the distal end 3 at the connection to connector unit 6'.

In this example and as described above in description of FIG. 2 the bending in direction of one flat outer surface region (arrow $B_u$) generates a torsion force T in the connector unit 6' due to larger bending diameter compared to the connector unit 6 and the tubular envelope 10. The tension force T can be transmitted to the distal end 3 as both the conductors 6, 6' and the tubular envelope are slidable relative to each other and the lead body 1. Therefore this tension force causes the lead body 1 to bend downwards in direction of arrow $B_d$. This mechanism is applicable for bending in direction of any of the three flat outer surface regions.

Deflecting the proximal end 2 of the lead in the direction of any of the three flat surfaces 13 leads to a very precise deflection at the distal end 3 in the direction of the opposite side. This effect is because "focusing" torsion force T at only one of the connector units 6, 6' or tubular envelope 10. So the implanter has precise control of deflection. A further advantage is made by the possibility to apply the mechanism in direction of any of the three flat outer surface regions. So the implanter can steer the lead in a three-dimensional manner As is not shown in the drawing figures the electrode leads UEL or BEL of FIGS. 1 and 3 can be provided with fixation means at the distal end known in the art, e.g. by means of small tines, a silicone helix or other friction-based means. A standard technique could be to "wedge" the electrode lead in place in a vessel matching to or smaller than the lead, even to the point of distending to adapt it to the diameter of the lead tip. Finally the distal end 3 can have a general J-shape as preform.

What is claimed is:

1. An electrode lead for implantation into a small heart vessel, or into a coronary sinus, comprising:

an elongated outer insulating lead body (1), having a proximal end (2), a distal end (3) and at least one electrode pole (4) at the distal end (3);

at least one electrical conductor unit (6, 6') for said at least one electrode pole (4), each of said at least one electrical conductor unit (6, 6') having a conductor core (7) and a separate insulating sheath (8) that surrounds said conductor core (7);

a lumen (9) in said elongated outer insulating lead body (1), that is defined by a tubular envelope (10), configured to accommodate a guide wire (11);

wherein the insulating sheath (8) that surrounds said at least one electrical conductor unit (6, 6') and the tubular envelope (10) of the lumen (9) are each in direct contact with each other and slidable relative to each other along their longitudinal direction (L) and fixed relative to each other in a vicinity of the distal end (3) of the elongated outer insulating lead body (1);

wherein the at least one electrical conductor unit (6, 6') and the tubular envelope (10) of the lumen (9) are configured in a side-by-side relationship parallel to each other, wherein an entirety of the at least one electrical conductor unit (6, 6') and the tubular envelope (10) of the lumen (9) are encased by, the elongated outer insulating lead body (1);

wherein said elongated outer insulating lead body (1) is configured to bend at said proximal end (2) in a first direction (Bu) which effects movement of the distal end of said elongated outer insulating lead body (1) in a second direction (Bd) that is opposite to said first direction when said at least one electrical conductor unit (6, 6') and said tubular envelope (10) move longitudinally with respect to one another wherein said insulating sheath (8) slides in direct contact with said tubular envelope (10);

wherein the elongated outer insulating lead body (1) includes at least one flat outer surface region; and, wherein the at least one electrical conductor unit (6, 6') and the tubular envelope (10) of the lumen (9) are fixed relative to each other in the vicinity of the proximal end (2) of the elongated outer insulating lead body (1).

2. The electrode lead according to claim 1, wherein the separate insulating sheath (8) of the at least one electrical conductor unit (6, 6') is made of PTFE polymer having a low friction surface.

3. The electrode lead according to claim 1, wherein the elongated outer insulating lead body (1) further comprises a low friction inner surface (12).

4. The electrode lead according to claim 3, wherein the elongated outer insulating lead body (1) is made of a silicone material and wherein said silicone material comprises a thin polyurethane coating as the low friction inner surface (12).

5. The electrode lead according to claim 1 configured as a unipolar electrode lead comprising one electrical conductor unit (6) and one tubular envelope (10) for a lumen (9) in a parallel side-by-side relationship, said unipolar electrode lead (UEL) having a substantially flat rectangular outer sectional contour.

6. The electrode lead according to claim 1 configured as a bipolar electrode lead comprising two electrical conductor units (6, 6') and one tubular envelope (10) for a lumen (9) in a parallel side-by-side relationship, said bipolar electrode lead (BEL) having a substantially triangular outer sectional contour.

7. An electrode lead for implantation into a small heart vessel, or into a coronary sinus, comprising:

an elongated outer insulating lead body (1), having a proximal end (2), a distal end (3) and at least one electrode pole (4) at the distal end (3);

at least one electrical conductor unit (6, 6') for said at least one electrode pole (4), each of said at least one electrical conductor unit (6, 6') having a conductor core (7) and a separate insulating sheath (8) that surrounds said conductor core (7);

a lumen (9) in said elongated outer insulating lead body (1), that is defined by a tubular envelope (10), configured to accommodate a guide wire (11);

wherein the insulating sheath (8) that surrounds said at least one electrical conductor unit (6, 6') and the tubular envelope (10) of the lumen (9) are each in direct contact with each other and slidable relative to each other along their longitudinal direction (L) and fixed relative to each other in a vicinity of the distal end (3) of the elongated outer insulating lead body (1);

wherein the at least one electrical conductor unit (6, 6') and the tubular envelope (10) of the lumen (9) are configured in a side-by-side relationship parallel to each other, wherein an entirety of the at least one electrical conductor unit (6, 6') and the tubular envelope (10) of the lumen (9) are encased by, the elongated outer insulating lead body (1);

wherein said elongated outer insulating lead body (1) is configured to bend at said proximal end (2) in a first direction (Bu) which effects movement of the distal end of said elongated outer insulating lead body (1) in a second direction (Bd) that is opposite to said first direction when said at least one electrical conductor unit (6, 6') and said tubular envelope (10) move longitudinally with respect to one another wherein said insulating sheath (8) slides in direct contact with said tubular envelope (10); and wherein the at least one electrical conductor unit (6, 6') and the tubular envelope (10) of the lumen (9) are fixed relative to each other in the vicinity of the proximal end (2) of the elongated outer insulating lead body (1).

8. The electrode lead according to claim 7, wherein the elongated outer insulating lead body (1) comprises flat outer surface regions (13).

9. The electrode lead according to claim 7, wherein the separate insulating sheath (8) of the at least one electrical conductor unit (6, 6') is made of PTFE polymer having a low friction surface.

10. The electrode lead according to claim 7, wherein the elongated outer insulating lead body (1) further comprises a low friction inner surface (12).

11. The electrode lead according to claim 10, wherein the elongated outer insulating lead body (1) is made of a silicone material and wherein said silicone material comprises a thin polyurethane coating as the low friction inner surface (12).

12. The electrode lead according to claim 7 configured as a unipolar electrode lead comprising one electrical conductor unit (6) and one tubular envelope (10) for a lumen (9) in a parallel side-by-side relationship, said unipolar electrode lead (UEL) having a substantially flat rectangular outer sectional contour.

13. The electrode lead according to claim 7 configured as a bipolar electrode lead comprising two electrical conductor units (6, 6') and one tubular envelope (10) for a lumen (9) in a parallel side-by-side relationship, said bipolar electrode lead (BEL) having a substantially triangular outer sectional contour.

14. An electrode lead for implantation into a small heart vessel, or into a coronary sinus, comprising:

an elongated outer insulating lead body (1), having a proximal end (2), a distal end (3) and at least one electrode pole (4) at the distal end (3);

at least one electrical conductor unit (6, 6') for said at least one electrode pole (4), each of said at least one electrical conductor unit (6, 6') having a conductor core (7) and a separate insulating sheath (8) that surrounds said conductor core (7);

a lumen (9) in said elongated outer insulating lead body (1), that is defined by a tubular envelope (10), configured to accommodate a guide wire (11);

wherein the insulating sheath (8) that surrounds said at least one electrical conductor unit (6, 6') and the tubular envelope (10) of the lumen (9) are each in direct contact with each other and slidable relative to each other along their longitudinal direction (L) and fixed relative to each other in a vicinity of the distal end (3) of the elongated outer insulating lead body (1);

wherein the at least one electrical conductor unit (6, 6') and the tubular envelope (10) of the lumen (9) are configured in a side-by-side relationship parallel to each other, wherein an entirety of the at least one electrical conductor unit (6, 6') and the tubular envelope (10) of the lumen (9) are encased by, the elongated outer insulating lead body (1);

wherein said elongated outer insulating lead body (1) is configured to bend at said proximal end (2) in a first direction (Bu) which effects movement of the distal end of said elongated outer insulating lead body (1) in a second direction (Bd) that is opposite to said first direction when said at least one electrical conductor unit (6, 6') and said tubular envelope (10) move longitudinally with respect to one another wherein said insulating sheath (8) slides in direct contact with said tubular envelope (10);

wherein the elongated outer insulating lead body (1) comprises flat outer surface regions (13);

wherein the at least one electrical conductor unit (6, 6') and the tubular envelope (10) of the lumen (9) are fixed relative to each other in the vicinity of the proximal end (2) of the elongated outer insulating lead body (1);

wherein the separate insulating sheath (8) of the at least one electrical conductor unit (6, 6') is made of PTFE polymer having a low friction surface; and, wherein the elongated outer insulating lead body (1) further comprises a low friction inner surface (12).

15. The electrode lead according to claim 14 configured as a unipolar electrode lead comprising one electrical conductor unit (6) and one tubular envelope (10) for a lumen (9) in a parallel side-by-side relationship, said unipolar electrode lead (UEL) having a substantially flat rectangular outer sectional contour.

16. The electrode lead according to claim 14 configured as a bipolar electrode lead comprising two electrical conductor units (6, 6') and one tubular envelope (10) for a lumen (9) in a parallel side-by-side relationship, said bipolar electrode lead (BEL) having a substantially triangular outer sectional contour.

* * * * *